(12) United States Patent
Nakada et al.

(10) Patent No.: US 6,316,682 B1
(45) Date of Patent: *Nov. 13, 2001

(54) PROCESS FOR PREPARING 1,1,1,3,3-PENTAFLUOROPROPANE

(75) Inventors: Tatsuo Nakada; Takashi Shibanuma; Yamamoto Akinori, all of Settsu (JP)

(73) Assignee: Daikin Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,609

(22) PCT Filed: Mar. 21, 1997

(86) PCT No.: PCT/JP97/00956

§ 371 Date: Nov. 30, 1998

§ 102(e) Date: Nov. 30, 1998

(87) PCT Pub. No.: WO97/45388

PCT Pub. Date: Dec. 4, 1997

(30) Foreign Application Priority Data

May 31, 1996 (JP) .................................................. 8/160776

(51) Int. Cl.⁷ .................................................. C07C 17/20

(52) U.S. Cl. .............................................................. 570/170
(58) Field of Search ................................................ 570/170

(56) References Cited

FOREIGN PATENT DOCUMENTS 2-207038   8/1990   (JP) .
WO 90/08754   8/1990   (WO) .

*Primary Examiner*—Alan Siegel
(74) *Attorney, Agent, or Firm*—Armstrong, Westerman, Hattori, McLeland & Naughton LLP

(57) ABSTRACT

A method of producing 1,1,1,3,3-pentafluoropropane wherein 1,1,1,3,3-pentafluoropropane is obtained by reacting at least one selected from the group consisting of fluorinated and chlorinated propane and chlorinated propane expressed by a general formula of $CX_3CH_2CHX_2$ (where X in this general formula indicates either a fluorine atom or a chlorine atom, but all of X's can never represent fluorine atoms at the same time) with a fluorinated antimony chloride. There is provided an economical and efficient method of producing 1,1,1,3,3-pentafluoropropane with high yield, which is an alternative compound to CFC's and HCFC's and is important in industry as a blowing agent, a refrigerant, a detergent, and a propellant that does not destroy the ozone in the ozone layer.

6 Claims, 1 Drawing Sheet

PROCESS FOR PREPARING 1,1,1,3,3-PENTAFLUOROPROPANE

This application is a 371 of PCT/JP97/00956 filed Mar. 21, 1997.

APPLICABLE INDUSTRIAL FIELDS

The present invention relates to a method of producing 1,1,1,3,3-pentafluoropropane, which is an alternative compound to CFC's and HCFC's and is important in industry as a blowing agent, a refrigerant, a detergent, and a propellant that does not destroy the ozone in the ozone layer.

PRIOR ART

As to the method of producing 1,1,1,3,3-pentafluoropropane (hereinafter referred to as HFC-245fa), the following methods are known: a method of obtaining HFC-245fa (WO 95/04022) in which 1,1,1,3,3,3-hexachloropropane, obtained by the addition of carbon tetrachloride and vinylidene chloride, is fluorinated to produce 1,1,1,3,3-pentafluoro-3-chloropropane. Next, the obtained 1,1,1,3,3-pentafluoro-3-chloropropane is reduced with hydrogen to produce HFC-245fa. Also a method of obtaining HFC-245fa (EP 0611744) by hydrogen reduction of 1,1,1,3,3-pentafluoro-2,3-dichloropropane or 1,1,1,3,3-pentafluoro-2,2,3-trichloropropane.

Both of these methods, however, require 2 processes: a fluorination process to obtain a precursor by fluorinating chlorides and a reduction process to reduce the obtained compound with hydrogen. Consequently, they have the disadvantage of being industrially inferior in terms of economic efficiency and the like because of the length of time taken by these processes.

Furthermore, because the hydrogen fluoride (hereinafter referred to as HF) yielded in the fluorination process forms a minimum azeotropic composition of about 1:1 mole with HFC-245fa, if any HF exists in the reaction system, unreacted HF will form an azeotrope with the HFC-245fa, which must then be removed from the system.

The HF is separated from HFC-245fa by a commonly known method and is recovered or discarded. That is, although HF is separated by a liquid separation operation, the inventors of the present invention has made it clear that the liquid separation of the azeotrope cannot be performed when the quantity of HF is large.

Moreover, in the case of washing with water, because the HF contained in an azeotrope is discarded as it is, there is a large loss of HF in this process. Besides, although it is possible to extract HF, when the quantity of HF is large, the economic efficiency of the method is reduced, resulting in high costs for the recovery of HF.

There is another known method of producing HFC-245fa, used to obtain HFC-245fa (WO 96/01797). In this method, 1,1,1,3,3-pentachloropropane is obtained by a reaction from the addition of carbon tetrachloride and vinyl chloride, and is then fluorinated with HF in the presence of a fluorination catalyst to produce HFC-245fa.

In this method, however, because the HFC-245fa produced forms an azeotropic composition with the unreacted HF, it is difficult to separate HFC-245fa, and the cost of purifying it is prohibitive, as mentioned above. Consequently, this method cannot be called an economically profitable method.

OBJECT OF THE INVENTION

The object of the present invention is to provide an economical method of producing HFC-245fa with superior selectivity, which is an alternative compound to CFC's and HCFC's and is important in industry as a blowing agent, a refrigerant, a detergent, and a propellant that does not destroy ozone in the ozone layer.

CONSTITUTION OF THE INVENTION

After carefully studying the methods of producing HFC-245fa in order to solve the above-mentioned problems, the inventors of the present invention found that HFC-245fa in particular, can be easily formed by reacting readily available 1,1,1,3,3-pentachloropropane with a fluorinated antimony chloride under conditions that exclude hydrogen fluoride; and further that HFC-245fa can be obtained with high selectivity by maintaining the amount of fluorine in the fluorinated antimony chloride, and by adequately controlling the reaction conditions.

As a result, the inventors found a method of economically producing HFC-245fa in high yields using only a fluorination process of a chloride as the raw material (that is, without the need for a hydrogen reduction process), resulting in the completion of the present invention.

That is, the present invention consists of a method of producing 1,1,1,3,3-pentafluoropropane in which 1,1,1,3,3-pentafluoropropane is obtained by reacting at least one selected from the group consisting of fluorinated and chlorinated propane and chlorinated propane, expressed by a general formula of $CX_3CH_2CHX_2$ (where X in this general formula indicates either a fluorine atom or a chlorine atom; however, all of X's can never represent fluorine atoms at the same time) with a fluorinated antimony chloride.

When producing 1,1,1,3,3-pentafluoropropane (HFC-245fa) using the method of the present invention, it is especially important to carry out the reaction in the absence of HF. That is, since HFC-245fa forms a minimum azeotrope of about 1:1 mole with HF as mentioned above, if HF exists in the system, unreacted HF will form an azeotrope with the HFC-245fa that has been produced, and this will be discharged from the system together with the HFC-245fa. When the quantity of such HF is larger than those of azeotrope composition, liquid separation between HF and HFC-245fa cannot be performed.

Accordingly, in the present invention, without providing any of HF into a reactor HFC-245fa can be obtained as a product. HFC-245fa product is obtained as an organic composition, and substantially does not contain HCl or HF, through a reaction using a fluorinated antimony chloride (liquid in a reactive condition) as a source of fluorine. In this way, HFC-245fa can be efficiently obtained without operations of separation, recovery and discard of HF.

In the method of the present invention, fluorinated antimony chlorides, obtained by fluorinating antimony pentachloride or antimony trichloride can be used as fluorinating agents.

Those fluorinated antimony chlorides in which antimony is pentavalent or trivalent can be used independently or as a mixture. These fluorinated antimony chlorides can be used without any trouble if the materials of the reactor are properly selected.

It is preferable that the fluorinated antimony chlorides to be used in the reaction are fluorinated by hydrogen fluoride in order to maintain their fluorine content (because the fluorine content reduces as the reaction progresses).

Practically, the method is outlined in FIG. 1. A second reactor (Reactor (2)) is installed separate from a first reactor (Reactor (1)) in which the product (HFC-245fa) is to be produced.

A fluorinated antimony chloride (10), with lowered fluorine content (supplied for the reaction in Reactor (1)) is introduced into Reactor (2), and regenerated there by adding hydrogen fluoride (5). Next, the regenerated fluorinated antimony chloride (11) is returned to Reactor 1.

The regeneration of the fluorinated antimony chloride can be performed continuously, however, it is not restricted to a such way.

Moreover, it is also possible to conduct the formation reaction of HFC-245fa and the regeneration reaction of the fluorinated antimony chloride by turns in one reactor.

In the method of the present invention, no special solvent is needed but it is also possible to use a known reaction solvent if necessary. Any solvent, as long as it is inert to a fluorinating agent (a fluorinated antimony chloride), can be used as such.

In the method of the present invention, although the reaction temperature is not critical, a convenient reaction temperature range is between 50° C. and 200° C. and is preferably between 60° C. and 180° C.

Furthermore, in the method of the present invention, though the reaction pressure is not critical, a convenient reaction pressure is between atmospheric pressure and 30 kg/cm$^2$G, and preferably is between atmospheric pressure and 20 kg/cm$^2$G.

Though the reaction products obtained by the present invention vary according to the reaction conditions, when 1,1,1,3,3-pentachloropropane (240fa) is used as the basic raw material, besides HFC-245fa, insufficiently fluorinated products, including fluorotetrachloropropane (HCFC-241 containing isomers), difluorotrichloropropane (HCFC-242 containing isomers), trifluorodichloropropane (HCFC-243 containing isomers) and tetrafluorochloropropane (HCFC-244 containing isomers), are obtained.

These insufficiently fluorinated products can be separated from the reaction mixture and recycled back into the fluorination reactor. In FIG. 1, such products (8) can be effectively utilized preferably by separating them from the reaction mixture (9) in Separator (3) and recycling them in Reactor (1), the fluorination reactor.

Moreover, recycling is also possible by using the following method. A fractionating column can be directly attached in the fluorination Reactor (1) to separate HFC-245fa, the objective product and to directly return insufficiently fluorinated by-products (having higher boiling points than that of HFC-245fa) to Reactor (1).

1,1,1,3,3-pentachloropropane, which can be used as the initial raw material in the present invention, can be easily obtained by addition reaction of carbon tetrachloride and vinyl chloride (Journal of Molecular Catalysis, Vol. 77, Page 51, 1992, and [KOGYO KAGAKU ZASSHI] Vol.72 No.7, Page 1526, 1969.).

As to the type of reaction in the method of the present invention, it is possible to adopt (a) a batch-type reaction in which, after the necessary raw materials are fed into one-time, the reaction is carried out and products and the like are recovered; (b) a semi-batch-type reaction, in which one of the raw materials is fed continuously; or (c) a continuous-type reaction in which raw materials are continuously fed in and products and the like are continuously taken out.

FIG. 1 shows a schematic flow of an example of a reaction apparatus usable in the method of the present invention. Compounds (9) produced in Reactor (1) where the fluorination reaction is conducted, are separated into an objective product (7) and by-products (8) in the Separator (3). The by-products (8) are returned (recycled) into Reactor (1), into which initial raw materials (4) can be appropriately fed.

Furthermore, fluorinated antimony chloride (10) (whose fluorine content was lowered in Reactor (1)) is activated (regenerated) in Reactor (2), which is present in order to activate the fluorinating agent, to maintain the fluorine content, and the regenerated fluorinated antimony chloride (11) can be returned to Reactor (1).

In Reactor (2), hydrogen fluoride (5) can be supplemented, and the generated HCl and other impurities can be removed from the reactor.

In addition, besides the above-mentioned methods, it is possible to adopt a method in which the objective HFC-245fa is not taken out the separator (3) but is returned to Reactor (1) together with any by-products (8). This operation can be repeated until the selectivity of the objective product is improved.

INDUSTRIAL APPLICABILITY

According to the method of the present invention, HFC-245fa can be obtained in high selectivity by reacting at least one selected from the group consisting of fluorinated and chlorinated propane and chlorinated propane, expressed by a general formula $CX_3CH_2CHX_2$ (where X in this general formula indicates either a fluorine atom or a chlorine atom, but all of X's can never represent fluorine atoms at the same) (the initial raw material in the examples in this specification, especially 1,1,1,3,3-pentachloropropane) with a fluorinated antimony chloride. In this way the objective product can be efficiently obtained from the reaction system.

As a result, through simplifying the production process and the purification process, the present invention can offer a production method in which HFC-245fa can be economically obtained and in high yield utilizing only a fluorinating process of a fluorinated and chlorinated propane and/or a chlorinated propane as initial raw materials, with the use of a fluorinated antimony chloride as a catalyst (a fluorinating agent), and without the use of any hydrogen reduction process.

Figure 1:
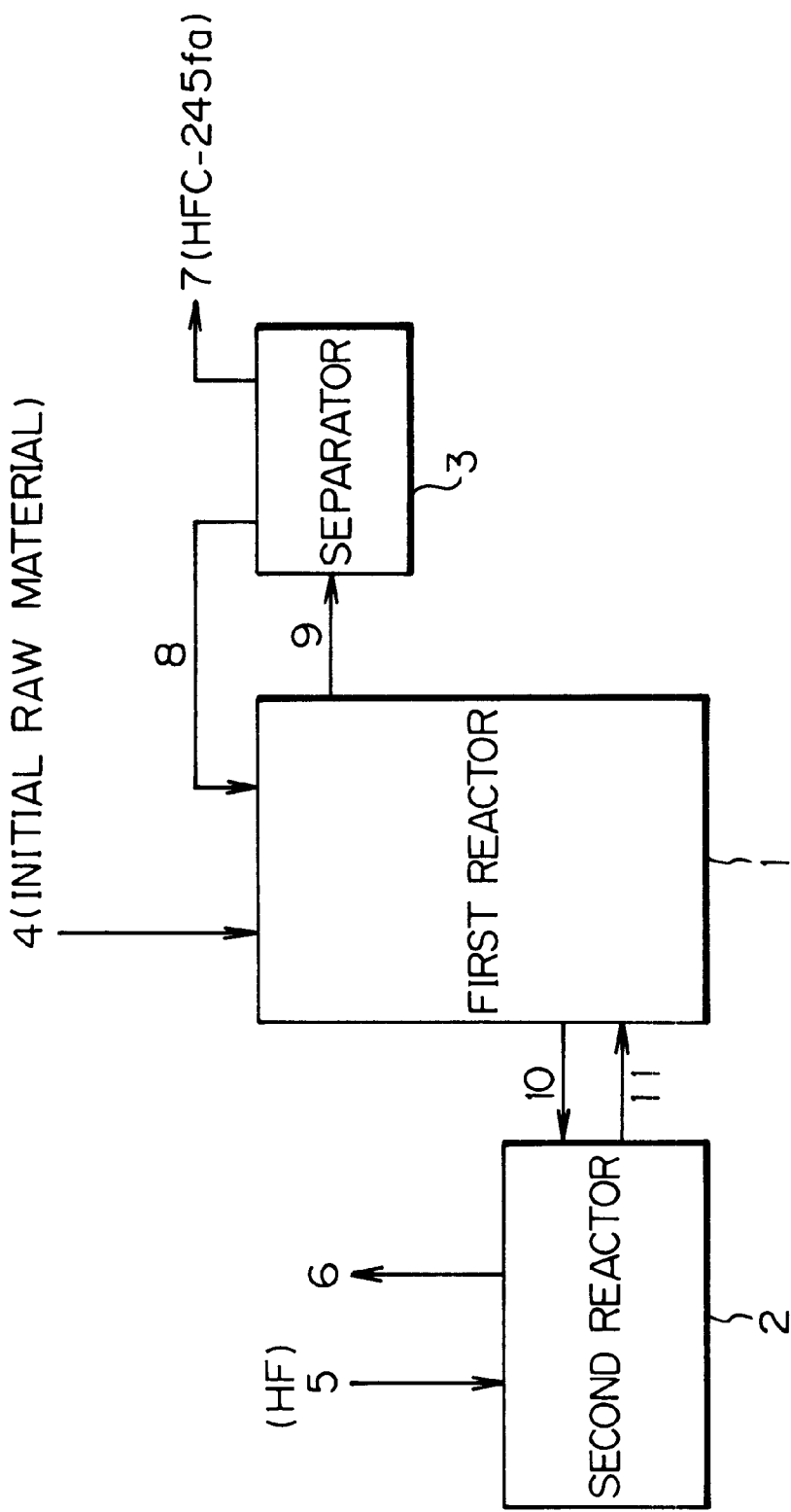
FIG. 1 is a flow diagram showing an example of the reaction apparatuses that can be used in producing 1,1,1,3,3-pentafluoropropane based on the present invention.

DESCRIPTION OF THE SYMBOLS (1) First reactor
(2) Second reactor
(3) Separator
(4) Initial raw material
(5) Hydrogen fluoride
(6) Impurities
(7) Objective product (HFC-245fa)
(8) By-products
(9) Reaction products
(10) Fluorinated antimony chloride whose fluorine content has been lowered
(11) Activated (regenerated) fluorinated antimony chloride

EXAMPLES

Concrete examples of the present invention will be explained in the following description, but the present invention should not be limited to the following examples.

Example 1

In a 500 ml autoclave with a condenser, 249.5 g (1.0 mole) of $SbCl_2F_3$ was placed and kept at 80° C. The condenser was kept at room temperature (20° C.). In the autoclave, 43.3 g (0.2 mole) of 1,1,1,3,3-pentachloropropane was introduced for 2 hours.

The gases produced at normal pressure were collected in dry ice-acetone trap. The quantity of the collected organic compounds was 23.8 g. Of the produced gases, only small quantities of HCl (0.03 g or less) and HF (0.03 g or less) were found.

The collected organic compounds were analyzed using gas phase-liquid phase chromatography (GLC). Using a Shimazu GC14A (made by Shimazu Corp.) and a 3 m long column filled with Porapack Q (made by GL Science Co.), an analysis was conducted at temperature conditions starting at 100° C. and rising by 10° C./min. for 4 minutes. The results are shown below:

| Retention time | Production ratio (Peak area ratio) | Product |
|---|---|---|
| 8.64 min. | 0.2% | $CF_3CH=CHF$ |
| 10.62 min. | 74.8% | $CF_3CH_2CHF_2$ (HFC-245fa) |
| 13.65 min. | 0.5% | $CF_3CH=CHCl$ |
| 15.39 min. | 4.3% | $CF_3CH_2CHFCl$ |
| 17.71 min. | 3.2% | $CF_3CCl=CHCl$ |
| 20.14 min. | 17.0% | $CF_3CH_2CHCl_2$ |

Because $CF_3CH=CHCl$, $CF_3CH_2CHFCl$, and $CF_3CH_2CHCl_2$ can be recycled into the autoclave, the objective product, HFC-245fa, in view of including reaction products caused by the recycling, was obtained with a selectivity of 95.5%.

Example 2

In a 500 ml autoclave with a condenser, 249.5 g (1.0 mole) of $SbCl_2F_3$ was placed and kept at 100° C. The condenser was kept at room temperature (15° C.). In the autoclave, 43.3 g (0.2 mole) of 1,1,1,3,3-pentachloropropane was introduced for 2 hours.

The gases produced at normal pressure were collected in a dry ice-acetone trap. The quantity of the collected organic compounds was 24.6 g. Of the produced gases, only small quantities of HCl (0.03 g or less) and HF (0.03 g or less) were found.

In the same conditions as mentioned above, the collected organic compounds were analyzed using gas phase-liquid phase chromatography (GLC). The results are shown below:

| Retention time | Production ratio (Peak area ratio) | Product |
|---|---|---|
| 8.64 min. | 0.2% | $CF_3CH=CHF$ |
| 10.62 min. | 80.8% | $CF_3CH_2CHF_2$ (HFC-245f) |
| 13.65 min. | 0.5% | $CF_3CH=CHCl$ |
| 15.39 min. | 3.3% | $CF_3CH_2CHFCl$ |
| 17.71 min. | 5.2% | $CF_3CCl=CHCl$ |
| 20.14 min. | 10.0% | $CF_3CH_2CHCl_2$ |

Because $CF_3CH=CHCl$, $CF_3CH_2CHFCl$ and $CF_3CH_2CHCl_2$ can be recycled into the autoclave, the objective product, HFC-245fa, in view of including reaction products caused by the recycling, was obtained with a selectivity of 93.7%.

Example 3

In a 500 ml autoclave with a condenser, 266.0 g (1.0 mole) of $SbCl_3F_2$ and 59.5 g (0.33 mole) of $SbF_3$ were placed and kept at 80° C. The condenser was kept at room temperature (25° C.). In the autoclave, 43.3 g (0.2 mole) of 1,1,1,3,3-pentachloropropane was introduced for 2 hours.

The gases produced at normal pressure were collected in a dry ice-acetone trap. The quantity of the collected organic compounds was 23.5 g. Of the produced gases, only small quantities of HCl (0.03 g or less) and HF (0.03 g or less) were found.

In the same conditions as mentioned above, the collected organic compounds were analyzed by gas phase-liquid phase chromatography (GLC). The results are shown below:

| Retention time | Production ratio (Peak area ratio) | Product |
|---|---|---|
| 8.64 min. | 0.2% | $CF_3CH=CHF$ |
| 10.62 min. | 76.7% | $CF_3CH_2CHF_2$ (HFC-245fa) |
| 13.65 min. | 0.7% | $CF_3CH=CHCl$ |
| 15.39 min. | 4.3% | $CF_3CH_2CHFCl$ |
| 17.71 min. | 3.1% | $CF_3CCl=CHCl$ |
| 20.14 min. | 15.0% | $CF_3CH_2CHCl_2$ |

Because $CF_3CH=CHCl$, $CF_3CH_2CHFCl$ and $CF_3CH_2CHCl_2$ can be recycled into the above-mentioned autoclave, the objective product, HFC-245fa, in view of including reaction products caused by the recycling, was obtained with a selectivity of 95.9%.

Example 4

In a 500 ml autoclave with a condenser, 266.0 g (1.0 mole) of $SbCl_3F_2$ was placed and kept at 80° C. The condenser was kept at room temperature (20° C.). In the autoclave, 43.3 g (0.2 mole) of 1,1,1,3,3-pentachloropropane was introduced for 2 hours.

The gases produced at normal pressure were collected in a dry ice-acetone trap. The quantity of the collected organic compounds was 22.3 g. Of the produced gases, only small quantities of HCl (0.03 g or less) and HF (0.03 g or less) were found.

In the same conditions as mentioned above, the collected organic compounds were analyzed by gas phase-liquid phase. chromatography (GLC). The results are shown below:

| Retention time | Production ratio (Peak area ratio) | Product |
|---|---|---|
| 8.64 min. | 0.2% | $CF_3CH=CHF$ |
| 10.62 min. | 54.8% | $CF_3CH_2CHF_2$ (HFC-245f) |
| 13.65 min. | 0.5% | $CF_3CH=CHCl$ |
| 15.39 min. | 4.4% | $CF_3CH_2CHFCl$ |
| 17.71 min. | 13.3% | $CF_3CCl=CHCl$ |
| 20.14 min. | 26.8% | $CF_3CH_2CHCl_2$ |

Because $CF_3CH=CHCl$, $CF_3CH_2CHFCl$ and $CF_3CH_2CHCl_2$ can be recycled into the above-mentioned autoclave, the objective product, HFC-245fa, in view of including reaction products caused by the recycling, was obtained with a selectivity of 80.5%.

Example 5

After the end of the reaction in example 1, the inside of the reactor was reduced in pressure to remove the organic compounds remaining in the system. Then, 20 g (1.0 mole)

of HF was introduced into the reactor. Next, the temperature in the inside of the reactor was raised to 80° C., and HCl generated was removed.

Next, in a 500 ml autoclave with a condenser, 249.5 g (1.0 mole) of $SbCl_2F_3$ was placed and kept at 80° C. The condenser was kept at room temperature (20° C.). In the autoclave, 43.3 g (0.2 mole) of 1,1,1,3,3-pentachloropropane was introduced for 2 hours.

The gases produced at normal pressure were collected in a dry ice-acetone trap. The quantity of the collected organic compounds was 24.1 g. Of the produced gases, only small quantities of HCl (0.03 g or less) and HF (0.03 g or less) were found.

In the same conditions as mentioned above, the collected organic compounds were analyzed by gas phase-liquid phase chromatography (GLC). The results are shown below:

| Retention time | Production ratio (Peak area ratio) | Product |
| --- | --- | --- |
| 8.64 min. | 0.1% | $CF_3CH=CHF$ |
| 10.62 min. | 75.9% | $CF_3CH_2CHF_2$ (HFC-245fa) |
| 13.65 min. | 0.3% | $CF_3CH=CHCl$ |
| 15.39 min. | 3.5% | $CF_3CH_2CHFCl$ |
| 17.71 min. | 3.2% | $CF_3CCl=CHCl$ |
| 20.14 min. | 17.0% | $CF_3CH_2CHCl_2$ |

Because $CF_3CH=CHCl$, $CF_3CH_2CHFCl$ and $CF_3CH_2CHCl_2$ can be recycled into the above-mentioned autoclave, the objective product, HFC-245fa, in view of including reaction products caused by the recycling, was obtained with a selectivity of 95.5%.

In this example, it was observed that the fluorine content of $SbCl_2F_3$ can be maintained by treating with HF.

COMPARATIVE EXAMPLE 1

In a 500 ml autoclave with a condenser, 29.9 g (0.1 mole) of $SbCl_6$ was placed and cooled with dry ice. Into the autoclave, 200 g (10.0 mole) of HF was introduced and the temperature was gradually raised to 80° C. while removing the HCl that was formed. The condenser was kept at room temperature (20° C.). Into the autoclave, 43.3 g (0.2 mole) of 1,1,1,3,3-pentachloropropane was introduced for 2 hours.

The gases produced at normal pressure were washed with water and collected in a dry ice-acetone trap. After neutralizing the washing tower, the HF content of the gases was determined by measuring the concentration of fluorine ions.

The quantity of the collected organic compounds was 22.6 g. Together with this, 3.2 g (0.16 mole) of HF was obtained.

In the same conditions as mentioned above, the collected organic compounds were analyzed by gas phase-liquid phase chromatography (GLC). The results are shown below:

| Retention time | Production ratio (Peak area ratio) | Product |
| --- | --- | --- |
| 8.64 min. | 0.1% | $CF_3CH=CHF$ |
| 10.62 min. | 98.4% | $CF_3CH_2CHF_2$ (HFC-245fa) |

-continued

| Retention time | Production ratio (Peak area ratio) | Product |
| --- | --- | --- |
| 13.65 min. | 0.5% | $CF_3CH=CHCl$ |
| 15.39 min. | 0.3% | $CF_3CH_2CHFCl$ |
| 17.71 min. | 0.2% | $CF_3CCl=CHCl$ |
| 20.14 min. | 0.5% | $CF_3CH_2CHCl_2$ |

In this comparative example 1, because HFC-245fa and HF had formed an azeotrope, they could not be separated by distillation, and because they were in a homogenous phase, they could not be separated by liquid separation and so on.

From the results of the above examples, it has become clear that the objective product (HFC-245fa) can be obtained with a high selectivity by methods based on the present invention. As the catalyst to be used, fluorinated antimony chloride, which had been sufficiently fluorinated, has been found to be suitable.

What is claimed is:

1. A method of producing 1,1,1,3,3-pentafluoropropane, wherein 1,1,1,3,3-pentafluoropropane is obtained by reacting at least one selected from the group consisting of fluorinated and chlorinated propane and chlorinated propane, expressed by a general formula of $CX_3CH_2CHX_2$ (where X in this general formula indicates either a fluorine atom or a chlorine atom, but all of X's can never represent fluorine atoms at the same time) with a fluorinated antimony chloride.

2. A method as defined in claim 1, wherein as the fluorinated antimony chloride, a fluorinated antimony chloride in which antimony is pentavalent or trivalent, or a mixture of both, is used.

3. A method as defined in claim 1 or 2, wherein the fluorinated and chlorinated propane and/or the chlorinated propane is reacted with the fluorinated antimony chloride in a reactors and then the products yielded in that reaction are returned to the said reactor.

4. A method as defined in claim 1 or 2, wherein the fluorinated and chlorinated propane and/or the chlorinated propane is reacted with the fluorinated antimony chloride in a reactor, and then an objective product, 1,1,1,3,3-pentafluoropropane, is separated from the other products yielded in the reaction, and then the by-products are returned to the said reactor.

5. A method as defined in claim 1 or 2, wherein after the fluorinated antimony chloride has been provided for the reaction, the said fluorinated antimony chloride is fluorinated with hydrogen fluoride to maintain the fluorine content.

6. A method as defined in claim 5, wherein from a first reactor in which an objective product, 1,1,1,3,3-pentafluoropropane, is obtained by reacting the fluorinated and chlorinated propane and/or the chlorinated propane with the fluorinated antimony chloride, the said fluorinated antimony chloride is taken out after having been provided for the reaction, and then the taken-out fluorinated antimony chloride is fluorinated with hydrogen fluoride in a second reactor and then returned to the said first reactor.

* * * * *